United States Patent
Xu et al.

(10) Patent No.: US 9,952,102 B1
(45) Date of Patent: Apr. 24, 2018

(54) METHOD AND APPARATUS FOR CALIBRATING A COLOR MEASUREMENT INSTRUMENT

(71) Applicant: Datacolor Holding AG, Luzern (CH)

(72) Inventors: Zhiling Xu, Princeton Junction, NJ (US); Michael H. Brill, Kingston, NJ (US)

(73) Assignee: DATACOLOR, INC., Lawrenceville, NJ (US)

( * ) Notice: Subject to any disclaimer, the term of this patent is extended or adjusted under 35 U.S.C. 154(b) by 0 days.

(21) Appl. No.: 15/628,803

(22) Filed: Jun. 21, 2017

Related U.S. Application Data

(60) Provisional application No. 62/487,169, filed on Apr. 19, 2017.

(51) Int. Cl.
| | | |
|---|---|---|
| *G01N 21/25* | (2006.01) | |
| *G01J 3/52* | (2006.01) | |
| *G01J 3/02* | (2006.01) | |
| *G01J 3/46* | (2006.01) | |
| *G01J 3/51* | (2006.01) | |

(52) U.S. Cl.
CPC ............. *G01J 3/524* (2013.01); *G01J 3/0297* (2013.01); *G01J 3/46* (2013.01); *G01J 3/51* (2013.01); *G01N 21/25* (2013.01)

(58) Field of Classification Search
CPC ........ G01J 3/02; G01J 3/51; G01J 3/52; G01J 3/46; G01J 3/513; G01J 3/524; G01N 21/25; G01N 21/00
See application file for complete search history.

(56) References Cited

U.S. PATENT DOCUMENTS

| | | |
|---|---|---|
| 6,163,377 A | 12/2000 | Boles et al. |
| 8,284,400 B1 | 10/2012 | Hastings et al. |
| 8,395,638 B2 | 3/2013 | Shannon et al. |
| 8,717,567 B2 | 5/2014 | Shannon et al. |
| 9,163,990 B2 | 10/2015 | Lianza et al. |
| 2013/0057680 A1* | 3/2013 | Hesline ............... G01J 3/0264 348/135 |

* cited by examiner

*Primary Examiner* — Abdullahi Nur

(57) ABSTRACT

In one example, an electronic signal is received from a target color measurement instrument that includes a plurality of color channels. A response of the target color measurement instrument to a light emitted by a target light emitting device is extracted from the signal. The response is calibrated to minimize a difference between the response and an output of a color matching function of a standard observer. Calibrating includes multiplying the response by a calibration matrix. The calibration matrix combines measurements of a first plurality of lights from a tunable light source and measurements of a second plurality of lights from the target light emitting device. A first subset of the measurements of the first plurality and second plurality of lights are made by the target color measurement instrument and a second subset of the measurements of the first plurality and second plurality of lights are made by a reference spectroradiometer.

20 Claims, 3 Drawing Sheets

METHOD AND APPARATUS FOR CALIBRATING A COLOR MEASUREMENT INSTRUMENT

CROSS REFERENCE TO RELATED APPLICATIONS

This application claims the priority of U.S. Provisional Patent Application Ser. No. 62/487,169, filed Apr. 19, 2017, which is herein incorporated by reference in its entirety.

FIELD OF THE DISCLOSURE

The present invention generally relates to the measurement of color, and more specifically relates to the calibration of color measurement instruments for measuring the color of light emitting objects.

BACKGROUND

In order to measure the color of a light emitting object (e.g., a light emitting diode (LED) lamp, a computer monitor, a television, a projector, or the like), a color measuring instrument such as a colorimeter should be able to output color measurement values that correspond to the color matching functions (CMFs) of the standard observer (according to Commission internationale de l'éclairage (CIE 1931)).

It is very difficult, however, to design a color measurement instrument whose three sensors match the CMFs exactly. Typically, a mathematical transformation is used to transform measurements made by the sensors to CMF-matching values.

SUMMARY OF THE DISCLOSURE

In one example, an electronic signal is received from a target color measurement instrument that includes a plurality of color channels. A response of the target color measurement instrument to a light emitted by a target light emitting device is extracted from the signal. The response is calibrated to minimize a difference between the response and an output of a color matching function of a standard observer. Calibrating includes multiplying the response by a calibration matrix. The calibration matrix combines measurements of a first plurality of lights from a tunable light source and measurements of a second plurality of lights from the target light emitting device. A first subset of the measurements of the first plurality and second plurality of lights are made by the target color measurement instrument and a second subset of the measurements of the first plurality and second plurality of lights are made by a reference spectroradiometer.

In another example, a non-transitory computer-readable medium stores instructions which, when executed by a processor, cause the processor to perform operations. The operations include receiving an electronic signal from a target color measurement instrument, wherein the target color measurement instrument includes a plurality of color channels, extracting from the signal a response of the target color measurement instrument to a light emitted by a target light emitting device, and calibrating the response to minimize a difference between the response and an output of a color matching function of a standard observer. The calibrating includes multiplying the response by a calibration matrix, wherein the calibration matrix combines measurements of a first plurality of lights from a tunable light source and measurements of a second plurality of lights from the target light emitting device, and wherein a first subset of the measurements of the first plurality of lights and the second plurality of lights are made by the target color measurement instrument and a second subset of the measurements of the first plurality of lights and the second plurality of lights are made by a reference spectroradiometer.

In another example, a device includes a processor and a non-transitory computer-readable medium storing instructions which, when executed by the processor, cause the processor to perform operations. The operations include receiving an electronic signal from a target color measurement instrument, wherein the target color measurement instrument includes a plurality of color channels, extracting from the signal a response of the target color measurement instrument to a light emitted by a target light emitting device, and calibrating the response to minimize a difference between the response and an output of a color matching function of a standard observer. The calibrating includes multiplying the response by a calibration matrix, wherein the calibration matrix combines measurements of a first plurality of lights from a tunable light source and measurements of a second plurality of lights from the target light emitting device, and wherein a first subset of the measurements of the first plurality of lights and the second plurality of lights are made by the target color measurement instrument and a second subset of the measurements of the first plurality of lights and the second plurality of lights are made by a reference spectroradiometer.

BRIEF DESCRIPTION OF THE DRAWINGS

The teachings of the present disclosure can be readily understood by considering the following detailed description in conjunction with the accompanying drawings, in which.

DETAILED DESCRIPTION

In one example, the present invention includes a software program for calibrating a multi-channel color measurement instrument so that a difference between the instrument outputs and the color matching functions of the standard observer (according to CIE 1931) is minimized. In one particular example, the present invention includes a software program for calibrating a multi-channel color measurement instrument so that, for a set of lights including lights from a tunable light source (e.g., a monochromator) and test lights from a set of target light sources (e.g., light sources of light emitting devices), a difference between the outputs of the multi-channel color measurement instrument and the XYZ tristimulus values of the standard observer (according to CIE 1931), as measured and computed by a reference spectroradiometer (also referred to herein as a "reference color measurement instrument"), is minimized.

In one example, the multi-channel color measurement instrument's measurements are calibrated through an n×3 calibration matrix, CM, where n is the number of channels in the multi-channel color measurement instrument, and 3 is the number of tristimulus values (e.g., X, Y, Z) in a color measurement. In one example, the calibration matrix CM is determined by first constructing a matrix CMF, where each row of the matrix CMF contains three tristimulus values for each spectral setting of the tunable light source, as measured by a reference spectroradiometer. The matrix CMF is appended with a matrix REF, where each row of the matrix REF contains three tristimulus values of a test light from the target light source, as measured by the reference spectroradiometer. Next, a matrix S is constructed, where each row of the matrix S contains the responses of the n channels of the multi-channel color measurement instrument to the outputs of one of the spectral settings of the tunable light source. The matrix S is then appended with a matrix R, where each row of the matrix R contains the responses of the multi-channel color measurement instrument to one of the test lights of the target light source. All of these matrices are combined by a computation that generates a calibration matrix CM.

Figure 1:
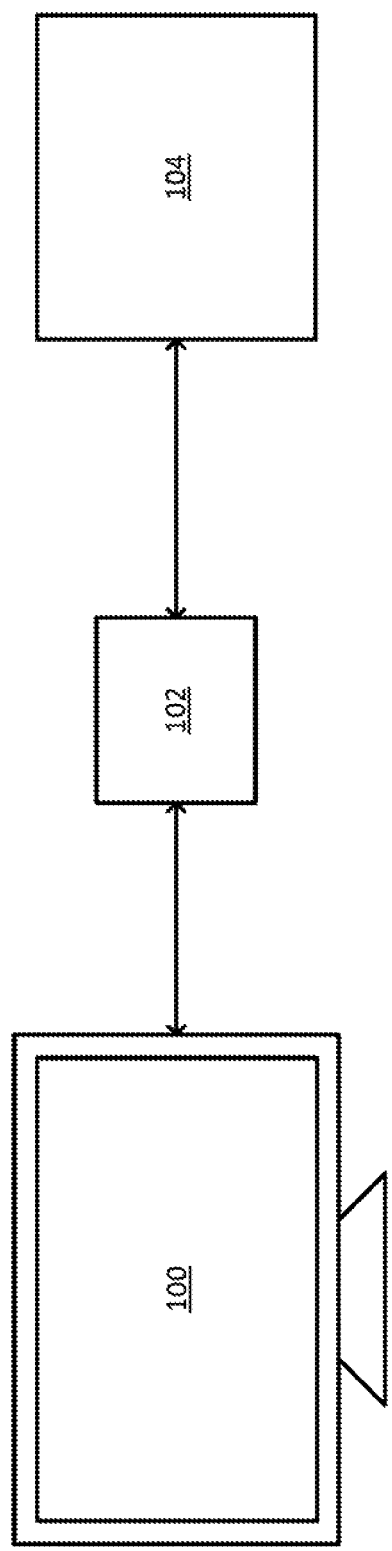
FIG. 1 is a schematic diagram illustrating one example of a system that may be adapted for use in accordance with the present disclosure.

FIG. 1 is a schematic diagram illustrating one example of a system that may be adapted for use in accordance with the present disclosure. The system generally includes a light emitting device 100, a color measurement instrument 102, and a calibration device 104.

In one example, the light emitting device 102 is an object or device that emits light in one or more colors, such as a liquid crystal display (LCD) television, a light emitting diode (LED) lamp, a computer monitor, a projector, or the like.

In one example, the color measurement instrument 102 is a colorimeter or similar device having n channels, where n is at least three. In one example, each channel comprises a filter/detector pair that is configured to detect emitted light of a particular wavelength or range of wavelengths.

The color measurement instrument 102 is coupled to the light emitting device 100. Coupling the color measurement instrument 102 to the light emitting device 100 may involve placing the color measurement instrument 102 in proximity with the light emitting device 100, so that the color measurement instrument 102 can sense the colors of the light emitted by the light emitting device 100. In this example, the coupling of the color measurement instrument 102 to the light emitting device 100 is non-permanent. In another example, however, the color measurement instrument 102 may be embedded (e.g., permanently) in the light emitting device 100. In this case, the color measurement instrument 102 may comprise a silicon chip fronted by a plurality of integral color filters and detectors.

The calibration device 104 may comprise a host computing device including a processor. For instance, the calibration device 104 may be configured as illustrated in FIG. 3, which is described in further detail below. The calibration device 104 is coupled (e.g., via a wired or wireless connection) to the color measurement instrument 102, so that the calibration device 104 can receive color measurement outputs (e.g., responses of the n color channels to various spectral settings of the light emitting device) from the color measurement instrument 102 (e.g., where the measurement outputs are encoded in electronic signals sent by the color measurement instrument 102 to the calibration device 104). The calibration device 104 may convert these color measurement outputs to values that match the color matching functions of the standard observer, as described in greater detail below in connection with FIG. 2.

Figure 2:
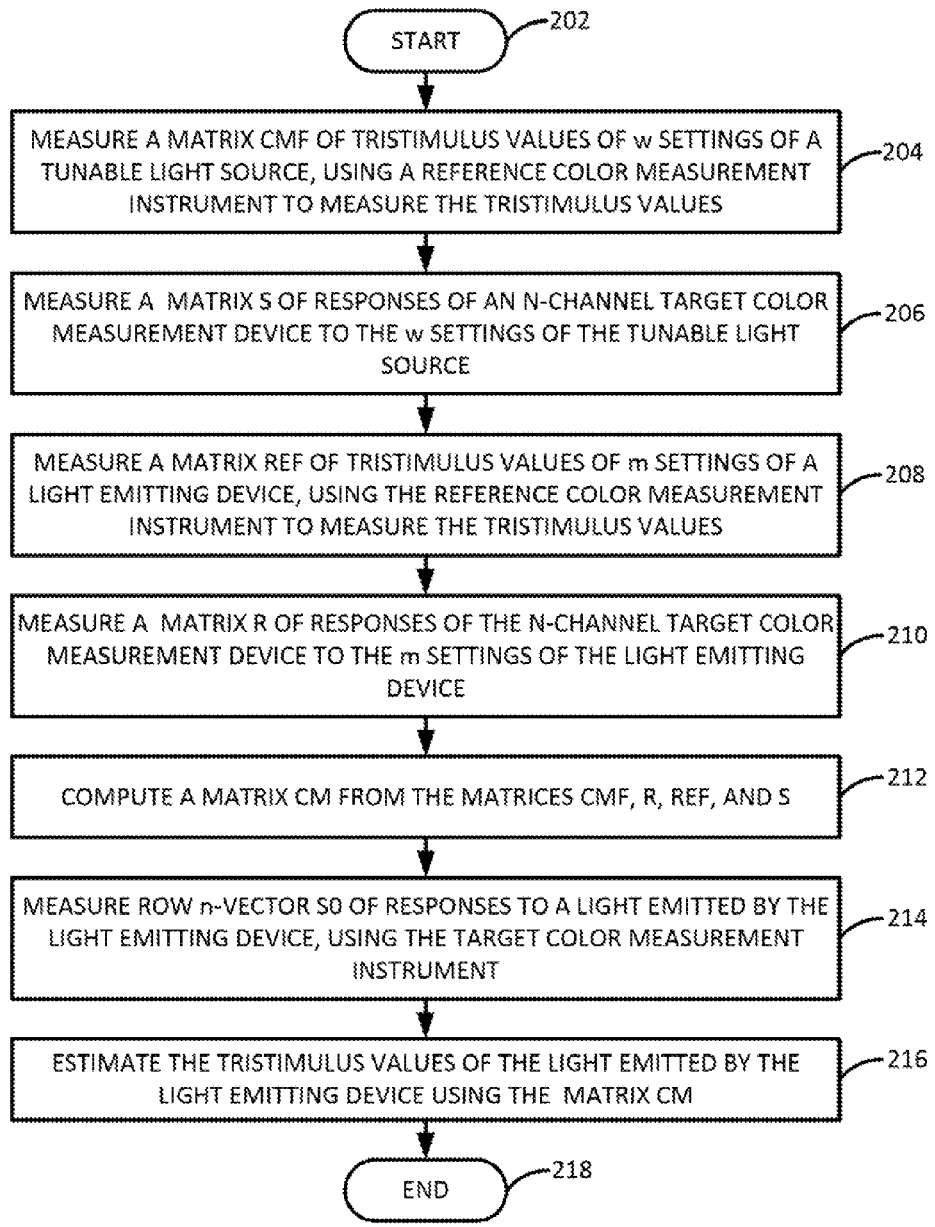
FIG. 2 is a flow chart illustrating one example of a method for calibrating a target color measurement instrument having n channels.
Figure 3:
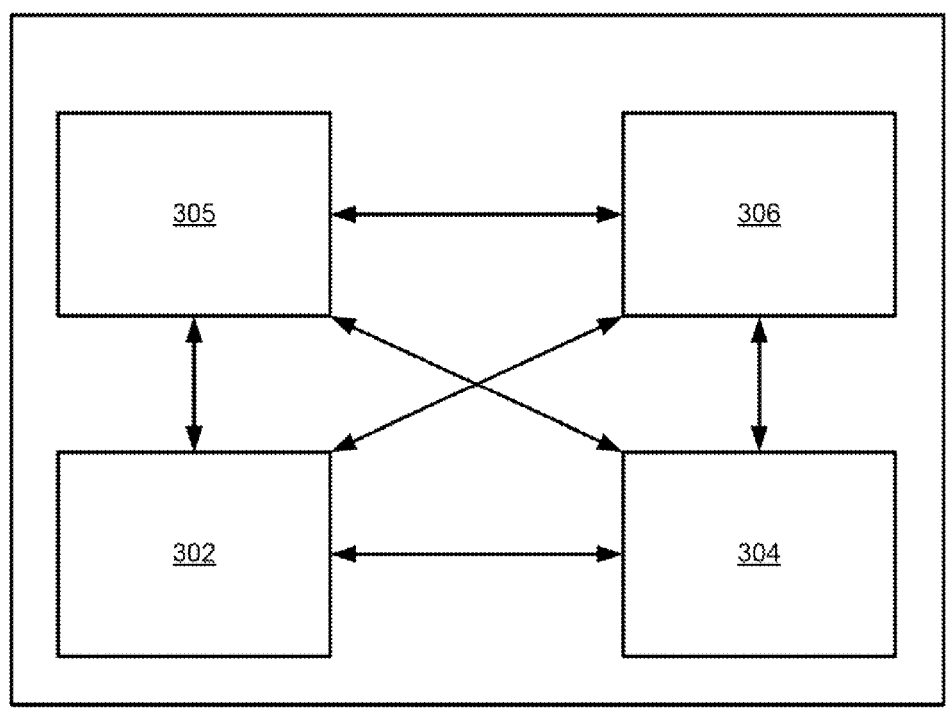
FIG. 3 is a high level block diagram of the calibration method that is implemented using a general purpose computing device.

FIG. 2 is a flow chart illustrating one example of a method 200 for calibrating a target color measurement instrument having n channels. In one example, n is greater than or equal to three. In one example, the method 200 may be performed, for instance, by the calibration device 104 of FIG. 1, using measurements provided by the target color measurement instrument (e.g., color measurement instrument 102) and by a reference color measurement instrument.

In one example, the method 200 constructs and employs a calibration matrix. The calibration matrix may be constructed by multiplying a first matrix by a Moore-Penrose pseudoinverse of a second matrix. In this case, both the first matrix and the second matrix are constructed using measurements of a first plurality of lights (from a tunable light source) and of a second plurality of lights (from a target light emitting device). In particular, the second matrix is constructed using a first subset of the measurements (made by the target color measurement instrument), while the first matrix is constructed using a second subset of the measurements (made by a reference spectroradiometer). The first matrix comprises a third matrix appended with a fourth matrix, while the second matrix comprises a fifth matrix appended with a sixth matrix, as described in further detail below.

The method 200 begins in step 202. In step 204, a matrix CMF (e.g., the third matrix referenced above) is measured. The matrix CMF contains the tristimulus values of a plurality of settings of a tunable light source as measured by a reference color measurement instrument. Thus, in one example, the matrix CMF is a w×3 matrix, where w is the number of spectral settings of the tunable light source and 3 is the number of measured XYZ tristimulus values of each setting of the w spectral settings. In one example, the reference color measurement instrument is a color measurement instrument that can produce as output XYZ tristimulus values that match the color matching functions of the standard observer, such as a spectroradiometer. The reference color measurement instrument may have any number of channels. In a further example, the tunable light source is a monochromator.

In step 206, a matrix S (e.g., the fifth matrix referenced above) is measured. The matrix S contains the channel responses of the target color measurement instrument to the plurality of settings of the tunable light source. Thus, in one example, the matrix S is a w×n matrix, where w is the number of spectral settings of the tunable light source and n is the number of channels of the target color measurement instrument. In this case, each element $S_{i,j}$ of the matrix S represents the response of the $i^{th}$ channel of the target color measurement instrument at the $j^{th}$ spectral setting of the tunable light source. In one example, the target color measurement instrument is a colorimeter.

In step 208, a matrix REF (e.g., the fourth matrix referenced above) is measured. The matrix REF contains the tristimulus values of a plurality of settings of a light emitting device as measured by the reference color measurement instrument. Thus, in one example, the matrix REF is an m×3 matrix, where m is the number of settings of the light emitting device and 3 is the number of measured XYZ tristimulus values of each setting of the m settings. In this case, each element $REF_{i,j}$ of the matrix REF represents the $j^{th}$ output (where j is a set of X, Y, Z tristimulus values) of the reference color measurement instrument in response to the $i^{th}$ setting of the light emitting device. In one example, the light emitting device is a device of a particular known make and model (e.g., a Brand X, Model Y light emitting diode television).

In step 210, a fourth matrix R (e.g., the sixth matrix referenced above) is measured. The matrix R contains the channel responses of the target color measurement instrument to the plurality of settings of the light emitting device.

Thus, in one example, the matrix R is an m×n matrix, where m is the number of settings of the light emitting device and n is the number of channels of the target color measurement instrument. In this case, each element $R_{i,j}$ of the matrix R represents the response of the $i^{th}$ channel of the target color measurement instrument to the $j^{th}$ setting of the light emitting device.

In step 212, a matrix CM, is computed from the matrices CMF, S, REF, and R measured in steps 204-210. The matrix CM is a calibration matrix. Thus, in one example, the matrix CM is an n×3 matrix, where n is the number of channels of the target color measurement instrument and 3 is the number of measured XYZ tristimulus values. In one example, the matrix CM may be computed from the matrices CMF, S, REF, and R, respectively, according to:

$$CM = pinv\begin{bmatrix} S \\ R \end{bmatrix} * \begin{bmatrix} CMF \\ REF \end{bmatrix} \quad \text{(EQN. 1)}$$

where pinv denotes the Moore-Penrose pseudoinverse, and EQN. 1 devolves from the optimized solution of:

$$\begin{bmatrix} S \\ R \end{bmatrix} * CM = \begin{bmatrix} CMF \\ REF \end{bmatrix} \quad \text{(EQN. 2)}$$

In this case, there is no need to perform wavelength numerical integration, because the equivalent is performed by the reference color measurement instrument to comprise the matrices CMF and REF. This is performed in an analogue manner by the target color measurement instrument to comprise the matrices S and R. Thus, in EQN. 1, the matrix S (the fifth matrix referenced above) is appended with the matrix R (the sixth matrix referenced above) to produce the second matrix referenced above, while the matrix CMF (the third matrix referenced above) is appended with the matrix REF (the fourth matrix referenced above) to produce the first matrix referenced above.

In step 214, the row n-vector S0 of responses to a light (e.g., any light) emitted by the light emitting device is measured, using the target color measurement instrument.

In step 216, the tristimulus values of a light (e.g., an arbitrary light) emitted by the target light emitting device (or another light emitting device) are estimated using the calibration matrix CM. In one example, the tristimulus values are estimated according to:

$$XYZ = S0 * CM \quad \text{(EQN. 3)}$$

Here, XYZ is the row 3-vector of the estimated XYZ tristimulus values of the light emitted by the target light emitting device, S0 is the row n-vector of the values measured by the target color measurement instrument, and CM is the n×3 calibration matrix defined above. Thus, by multiplying the output of the target color measurement instrument by the calibration matrix CM, one can convert the outputs of the target color measurement instrument to values that match the color matching functions of the standard observer (according to CIE 1931).

The method 200 ends in step 218.

Examples of the present disclosure may be generalized in various ways. For instance, the relation S*CM=CMF, which is an overdetermined matrix equation that allows one to calculate the calibration matrix, CM, can be modified by pre-multiplying the relation by a diagonal w×w square matrix, W, which weights the importances of the various wavelengths (e.g., settings of the light emitting device) that in the least square fit to find the calibration matrix, CM. In this case, W*S*CM=W*CMF.

In a further example, the diagonal square matrix, W, has dimensions of (w+m)×(w+m). In this case, the $k^{th}$ diagonal element represents the importance of the $k^{th}$ wavelength (e.g., setting of the light emitting device), whether it be represented in CMF or REF. Thus, EQNs. 1 and 2 can be respectively generalized as:

$$CM = pinv\left\{W * \begin{bmatrix} S \\ R \end{bmatrix}\right\} * W * \begin{bmatrix} CMF \\ REF \end{bmatrix} \quad \text{(EQN. 4)}$$

$$W * \begin{bmatrix} S \\ R \end{bmatrix} * CM = W * \begin{bmatrix} CMF \\ REF \end{bmatrix} \quad \text{(EQN. 5)}$$

where the diagonal elements of the diagonal square matrix, W, default to one unless another value demonstrates performance advantages. For instance, when measuring the colors of certain light emitting devices (e.g., where the geometry of the display lighting is sufficiently dissimilar from the geometry of a calibrated light source), it may be advantageous to set the elements of the diagonal square matrix, W, that multiply the matrix CMF to zero.

In a further example still, the square matrix, W, may be an arbitrary non-singular matrix of real numbers which is not necessarily a diagonal matrix.

Since the calibration matrix, CM, includes the information on a target type of light emitting device, CM will reduce the error, E, between the output of the n-channel target color measuring instrument and the output of the reference color measurement instrument.

In one example, where the n-channel target color measurement instrument is used to measure the colors of different types of light emitting devices, a device-specific matrix, S, may be stored for one or more of the different types of light emitting devices (e.g., in the light emitting device(s) or in the calibration device 104). A general matrix CMF may also be stored, as well as a matrix REF, and a matrix R for each type of light emitting device. Then, when the color of a specific type of light emitting device is being measured, its corresponding matrices REF and R, can be retrieved. Using EQNs. 1 and 3, above, the calibrated output color tristimulus values XYZ can be computed. The calibration matrix CM, can be pre-calculated and stored, or it can be calculated right before the output of the calibrated output color tristimulus values XYZ.

In one example, where there are no matrices REF and R, stored for the exact model of the light emitting device, the matrices REF and R for other models of the same type of light emitting device (e.g., LED lamp versus computer monitor) may be aggregated to form combined matrices.

FIG. 3 is a high level block diagram of the calibration method that is implemented using a general purpose computing device 300. In one example, a general purpose computing device 300 comprises a processor 302, a memory 304, a calibration module 305 and various input/output (I/O) devices 306 such as a display, a keyboard, a mouse, a modem, a network connection and the like. In one example, at least one I/O device is a storage device (e.g., a disk drive, an optical disk drive, a floppy disk drive). It should be understood that the calibration module 305 can be implemented as a physical device or subsystem that is coupled to a processor through a communication channel.

Alternatively, the calibration module 305 can be represented by one or more software applications (or even a combination of software and hardware, e.g., using Application Specific Integrated Circuits (ASIC)), where the software is loaded from a storage medium (e.g., I/O devices 306) and operated by the processor 302 in the memory 304 of the general purpose computing device 300. Additionally, the software may run in a distributed or partitioned fashion on two or more computing devices similar to the general purpose computing device 300. Thus, in one example, the calibration module 305 for calibrating a color measurement instrument described herein with reference to the preceding Figures can be stored on a computer readable medium or carrier (e.g., RAM, magnetic or optical drive or diskette, and the like).

It should be noted that although not explicitly specified, one or more steps of the methods described herein may include a storing, displaying and/or outputting step as required for a particular application. In other words, any data, records, fields, and/or intermediate results discussed in the methods can be stored, displayed, and/or outputted to another device as required for a particular application. Furthermore, steps or blocks in the accompanying Figures that recite a determining operation or involve a decision, do not necessarily require that both branches of the determining operation be practiced. In other words, one of the branches of the determining operation can be deemed as an optional step.

Although various examples which incorporate the teachings of the present disclosure have been shown and described in detail herein, those skilled in the art can readily devise many other varied examples that still incorporate these teachings.

What is claimed is:

1. A method, comprising:
   receiving an electronic signal from a target color measurement instrument, wherein the target color measurement instrument comprises a plurality of color channels;
   extracting from the signal a response of the target color measurement instrument to a light emitted by a target light emitting device; and
   calibrating the response to minimize a difference between the response and an output of a color matching function of a standard observer, wherein the calibrating comprises multiplying the response by a calibration matrix, wherein the calibration matrix combines measurements of a first plurality of lights from a tunable light source and measurements of a second plurality of lights from the target light emitting device, and wherein a first subset of the measurements of the first plurality of lights and the second plurality of lights are made by the target color measurement instrument and a second subset of the measurements of the first plurality of lights and the second plurality of lights are made by a reference spectroradiometer.

2. The method of claim 1, wherein the plurality of color measurement channels comprises at least three color measurement channels.

3. The method of claim 1 wherein the target color measurement instrument is a screen colorimeter.

4. The method of claim 1, wherein the tunable light source is a monochromator.

5. The method of claim 1, wherein the calibration matrix comprises an n×3 matrix, wherein n is a number of the plurality of color channels and 3 is a number of tristimulus values.

6. The method of claim 5, further comprising constructing the calibration matrix, wherein the constructing comprises:
   constructing a first matrix using the second subset of the measurements;
   constructing a second matrix using the first subset of the measurements; and
   multiplying the first matrix by a Moore-Penrose pseudo-inverse of the second matrix.

7. The method of claim 6, wherein constructing the first matrix comprises:
   measuring a third matrix, wherein each row of the third matrix contains three tristimulus values for one spectral setting of one light of the first plurality of lights, as measured by the reference spectroradiometer;
   measuring a fourth matrix, wherein each row of the fourth matrix contains three tristimulus values of one light of the second plurality of lights, as measured by the reference spectroradiometer; and
   appending the third matrix with the fourth matrix.

8. The method of claim 7, wherein constructing the second matrix comprises:
   measuring a fifth matrix, wherein each row of the fifth matrix contains three tristimulus values for one spectral setting of one light of the first plurality of lights, as measured by the target color measurement instrument;
   measuring a sixth matrix, wherein each row of the sixth matrix contains three tristimulus values of one light of the second plurality of lights, as measured by the target color measurement instrument; and
   appending the fifth matrix with the sixth matrix.

9. The method of claim 8, wherein the constructing the calibration matrix further comprises:
   multiplying each of the first matrix and the second matrix by a square matrix, where the square matrix weights relative importances of settings of the second plurality of lights from the target light emitting device.

10. The method of claim 9, wherein the square matrix is a diagonal square matrix.

11. The method of claim 9, wherein the square matrix is an arbitrary non-singular matrix of real numbers.

12. The method of claim 1, wherein the response comprises a row-n vector S0 of responses.

13. The method of claim 12, wherein the multiplying the response by a calibration matrix produces a row 3-vector of estimated XYZ tristimulus values of the light emitted by the target light emitting device.

14. A non-transitory computer-readable medium storing instructions which, when executed by a processor, cause the processor to perform operations, the operations comprising:
   receiving an electronic signal from a target color measurement instrument, wherein the target color measurement instrument comprises a plurality of color channels;
   extracting from the signal a response of the target color measurement instrument to a light emitted by a target light emitting device; and
   calibrating the response to minimize a difference between the response and an output of a color matching function of a standard observer, wherein the calibrating comprises multiplying the response by a calibration matrix, wherein the calibration matrix combines measurements of a first plurality of lights from a tunable light source and measurements of a second plurality of lights from the target light emitting device, and wherein a first subset of the measurements of the first plurality of lights and the second plurality of lights are made by the target color measurement instrument and a second subset of the measurements of the first plurality of lights and the second plurality of lights are made by a reference spectroradiometer.

15. The non-transitory computer-readable medium of claim 14, wherein the calibration matrix comprises an n×3 matrix, wherein n is a number of the plurality of color channels and 3 is a number of tristimulus values.

16. The non-transitory computer-readable medium of claim 15, further comprising constructing the calibration matrix, wherein the constructing comprises:
   constructing a first matrix using the second subset of the measurements;
   constructing a second matrix using the first subset of the measurements; and
   multiplying the first matrix by a Moore-Penrose pseudo-inverse of the second matrix.

17. The non-transitory computer-readable medium of claim 16, wherein constructing the first matrix comprises:
   measuring a third matrix, wherein each row of the third matrix contains three tristimulus values for one spectral setting of one light of the first plurality of lights, as measured by the reference spectroradiometer;
   measuring a fourth matrix, wherein each row of the fourth matrix contains three tristimulus values of one light of the second plurality of lights, as measured by the reference spectroradiometer; and
   appending the third matrix with the fourth matrix.

18. The non-transitory computer-readable medium of claim 17, wherein constructing the second matrix comprises:
   measuring a fifth matrix, wherein each row of the fifth matrix contains three tristimulus values for one spectral setting of one light of the first plurality of lights, as measured by the target color measurement instrument;
   measuring a sixth matrix, wherein each row of the sixth matrix contains three tristimulus values of one light of the second plurality of lights, as measured by the target color measurement instrument; and
   appending the fifth matrix with the sixth matrix.

19. The non-transitory computer-readable medium of claim 18, wherein the constructing the calibration matrix further comprises:
   multiplying each of the first matrix and the second matrix by a square matrix, where the square matrix weights relative importances of settings of the second plurality of lights from the target light emitting device.

20. A device, comprising: a processor; and a non-transitory computer-readable medium storing instructions which, when executed by the processor, cause the processor to perform operations comprising: receiving an electronic signal from a target color measurement instrument, wherein the target color measurement instrument comprises a plurality of color channels; extracting from the signal a response of the target color measurement instrument to a light emitted by a target light emitting device; and calibrating the response to minimize a difference between the response and an output of a color matching function of a standard observer, wherein the calibrating comprises multiplying the response by a calibration matrix, wherein the calibration matrix combines measurements of a first plurality of lights from a tunable light source and measurements of a second plurality of lights from the target light emitting device, and wherein a first subset of the measurements of the first plurality of lights and the second plurality of lights are made by the target color measurement instrument and a second subset of the measurements of the first plurality of lights and the second plurality of lights are made by a reference spectroradiometer.

* * * * *